(12) United States Patent
Lavelle et al.

(10) Patent No.: US 7,731,722 B2
(45) Date of Patent: Jun. 8, 2010

(54) URETERAL BACKSTOP FILTER AND RETRIEVAL DEVICE

(75) Inventors: Shay Lavelle, Annacotty (IE); Marvin O. Andrews, Bloomington, IN (US); Frank J. Fischer, Jr., Bloomington, IN (US); Walter N. Ryan, Bloomington, IN (US); Valery Diamant, Katzrin (IL); Stepan Khachin, Tomsk (RU); Nadezda Yasko, Tomsk (RU); Vladimir Khachin, Tomsk (RU)

(73) Assignees: Vance Products Incorporated, Spencer, IN (US); Lithotech Medical, Limited, Katzrin (IL)

( * ) Notice: Subject to any disclaimer, the term of this patent is extended or adjusted under 35 U.S.C. 154(b) by 303 days.

(21) Appl. No.: 10/902,754

(22) Filed: Jul. 28, 2004

(65) Prior Publication Data

US 2005/0043756 A1      Feb. 24, 2005

Related U.S. Application Data

(60) Provisional application No. 60/491,351, filed on Jul. 31, 2003.

(51) Int. Cl.
*A61B 17/22* (2006.01)
*A61M 29/00* (2006.01)
(52) U.S. Cl. ........................................ 606/127; 606/200
(58) Field of Classification Search ................ 606/200, 606/191, 106, 110, 113, 114, 127, 128; 604/104–107; 623/1.11
See application file for complete search history.

(56) References Cited

U.S. PATENT DOCUMENTS 3,472,230 A      10/1969   Fogarty
3,496,330 A      2/1970    Needham (Continued)

FOREIGN PATENT DOCUMENTS

EP      0428 998 A1      11/1990

(Continued)

OTHER PUBLICATIONS

Partial International Search Report from corresponding PCT Appl PCT/US2004/024430 dated Mar. 2, 2005.

(Continued)

*Primary Examiner*—Todd E Manahan
*Assistant Examiner*—Lindsey Bachman
(74) *Attorney, Agent, or Firm*—Brinks Hofer Gilson & Lione

(57) ABSTRACT

A retrieval device for use in renal, biliary, vascular or other systems of a body includes a collapsible basket in a narrow sheath. A surgeon advances the device beyond an object to be removed from a body, such as a kidneystone, a gallstone, or a thrombus. The surgeon then retracts the sheath or advances the basket from the sheath. The basket deploys only to one side of the sheath. In some embodiments, the periphery of the basket has a flex point to enable the basket to easily collapse into the sheath. If the sheath is adjacent a body vessel, such as a blood vessel or a ureter, the sheath remains adjacent the wall, while the device deploys in such a manner as to seal against the walls of the vessel and block the flow of fragments, emboli, thrombi, or other undesirable objects.

40 Claims, 11 Drawing Sheets

U.S. PATENT DOCUMENTS

| | | | |
|---|---|---|---|
| 3,996,938 A | 12/1976 | Clark, III | |
| 4,327,846 A | 5/1982 | Starp | |
| 4,347,846 A | 9/1982 | Dormia | |
| 4,486,680 A | 12/1984 | Bonnet et al. | |
| 4,611,594 A | 9/1986 | Grayhack et al. | |
| 4,625,726 A | 12/1986 | Duthoy | |
| 4,633,871 A | 1/1987 | Shinozuka | |
| 4,682,599 A | 7/1987 | Konomura | |
| 4,790,812 A | 12/1988 | Hawkins, Jr. et al. | |
| 4,807,626 A | 2/1989 | McGirr | |
| 4,873,978 A | 10/1989 | Ginsburg | |
| 4,955,385 A | 9/1990 | Kvalo et al. | |
| 5,057,114 A | 10/1991 | Wittich et al. | |
| 5,059,199 A | 10/1991 | Okada | |
| 5,064,428 A | 11/1991 | Cope et al. | |
| 5,100,423 A | 3/1992 | Fearnot | |
| 5,171,233 A | 12/1992 | Amplatz et al. | |
| 5,176,688 A | 1/1993 | Narayan et al. | |
| 5,190,555 A | 3/1993 | Wetter et al. | |
| 5,190,557 A | 3/1993 | Borodulin et al. | |
| 5,192,286 A | 3/1993 | Phan et al. | |
| 5,207,686 A | 5/1993 | Dolgin | |
| 5,234,439 A | 8/1993 | Wilk et al. | |
| 5,312,418 A | 5/1994 | Bonnett | |
| 5,329,942 A | 7/1994 | Gunther et al. | |
| 5,330,482 A | 7/1994 | Gibbs et al. | |
| 5,352,184 A | 10/1994 | Goldberg et al. | |
| 5,354,310 A | 10/1994 | Garnic et al. | |
| 5,403,324 A | 4/1995 | Ciervo et al. | |
| 5,449,372 A | 9/1995 | Schmaltz et al. | |
| 5,496,330 A | 3/1996 | Bates et al. | |
| 5,549,626 A | 8/1996 | Miller et al. | |
| 5,643,281 A | 7/1997 | Suhocki et al. | |
| 5,658,296 A | 8/1997 | Bates et al. | |
| 5,720,754 A | 2/1998 | Middleman et al. | |
| 5,749,883 A | 5/1998 | Halpern | |
| 5,769,816 A | 6/1998 | Barbut et al. | |
| 5,792,145 A | 8/1998 | Bates et al. | |
| 5,792,156 A | 8/1998 | Perouse | |
| 5,814,064 A | 9/1998 | Daniel et al. | |
| 5,846,260 A | 12/1998 | Maahs | |
| 5,848,864 A | 12/1998 | Selby | |
| 5,848,964 A | 12/1998 | Samuels | |
| 5,935,139 A | 8/1999 | Bates | |
| 5,941,896 A | 8/1999 | Kerr | |
| 5,989,266 A | 11/1999 | Foster | |
| 6,013,086 A | 1/2000 | Ouchi et al. | |
| 6,077,274 A | 6/2000 | Ouchi et al. | |
| 6,093,196 A | 7/2000 | Okada | |
| 6,096,053 A | 8/2000 | Bates | |
| 6,152,932 A | 11/2000 | Ternstrom | |
| 6,159,220 A * | 12/2000 | Gobron et al. | 606/127 |
| 6,168,603 B1 | 1/2001 | Leslie et al. | |
| 6,171,328 B1 | 1/2001 | Addis | |
| 6,179,861 B1 | 1/2001 | Khosravi et al. | |
| 6,182,482 B1 | 2/2001 | Issitt | |
| 6,183,482 B1 | 2/2001 | Bates et al. | |
| 6,187,017 B1 | 2/2001 | Gregory, Jr. | |
| 6,190,394 B1 | 2/2001 | Lind et al. | |
| 6,203,552 B1 | 3/2001 | Bagley et al. | |
| 6,203,561 B1 | 3/2001 | Ramee et al. | |
| 6,217,589 B1 | 4/2001 | McAlister | |
| 6,224,612 B1 | 5/2001 | Bates et al. | |
| 6,238,412 B1 | 5/2001 | Dubrul et al. | |
| 6,302,895 B1 | 10/2001 | Gobron et al. | |
| 6,319,261 B1 | 11/2001 | Bowers | |
| 6,346,116 B1 | 2/2002 | Brooks et al. | |
| 6,348,056 B1 | 2/2002 | Bates et al. | |
| 6,350,266 B1 | 2/2002 | White et al. | |
| 6,364,895 B1 | 4/2002 | Greenhalgh | |
| 6,368,328 B1 | 4/2002 | Chu et al. | |
| 6,371,970 B1 | 4/2002 | Khosravi et al. | |
| 6,371,971 B1 | 4/2002 | Tsugita et al. | |
| 6,375,670 B1 | 4/2002 | Greenhalgh | |
| 6,379,345 B1 | 4/2002 | Constantz | |
| 6,383,196 B1 | 5/2002 | Leslie et al. | |
| 6,402,761 B2 | 6/2002 | McAlister | |
| 6,500,182 B2 | 12/2002 | Foster | |
| 6,517,550 B1 | 2/2003 | Kónya et al. | |
| 6,589,263 B1 * | 7/2003 | Hopkins et al. | 606/200 |
| 6,610,077 B1 * | 8/2003 | Hancock, et al. | 606/200 |
| 6,676,682 B1 * | 1/2004 | Tsugita et al. | 606/200 |
| 6,740,061 B1 | 5/2004 | Oslund et al. | |
| 6,855,155 B2 * | 2/2005 | Denardo et al. | 606/200 |
| 7,101,380 B2 * | 9/2006 | Khachin et al. | 606/127 |
| 7,169,154 B1 * | 1/2007 | Que et al. | 606/127 |
| 2002/0068954 A1 | 6/2002 | Foster | |
| 2002/0123765 A1 | 9/2002 | Sepetka et al. | |
| 2003/0050663 A1 * | 3/2003 | Khachin et al. | 606/200 |
| 2004/0122445 A1 | 6/2004 | Butler et al. | |

FOREIGN PATENT DOCUMENTS

| | | | |
|---|---|---|---|
| EP | 0998 227 B1 | 5/2000 | |
| EP | 998227 B1 | 2/2004 | |
| WO | WO 97/41782 | 11/1997 | |
| WO | WO 98/29043 | 7/1998 | |
| WO | WO 98/36694 | 8/1998 | |
| WO | WO 99/53849 | 10/1999 | |
| WO | WO 01/05311 A1 | 1/2001 | |
| WO | WO 02/056943 A2 | 7/2002 | |
| WO | WO 02/056944 A2 | 7/2002 | |
| WO | WO 03/002006 | 1/2003 | |
| WO | WO 2004/056275 | 7/2004 | |
| WO | WO 2004/056275 A1 | 7/2004 | |

OTHER PUBLICATIONS

International Search Report dated May 26, 2005 for PCT Application No. PCT/US2004/024430.

US 6,348,062, 02/2002, Hopkins et al. (withdrawn)

* cited by examiner

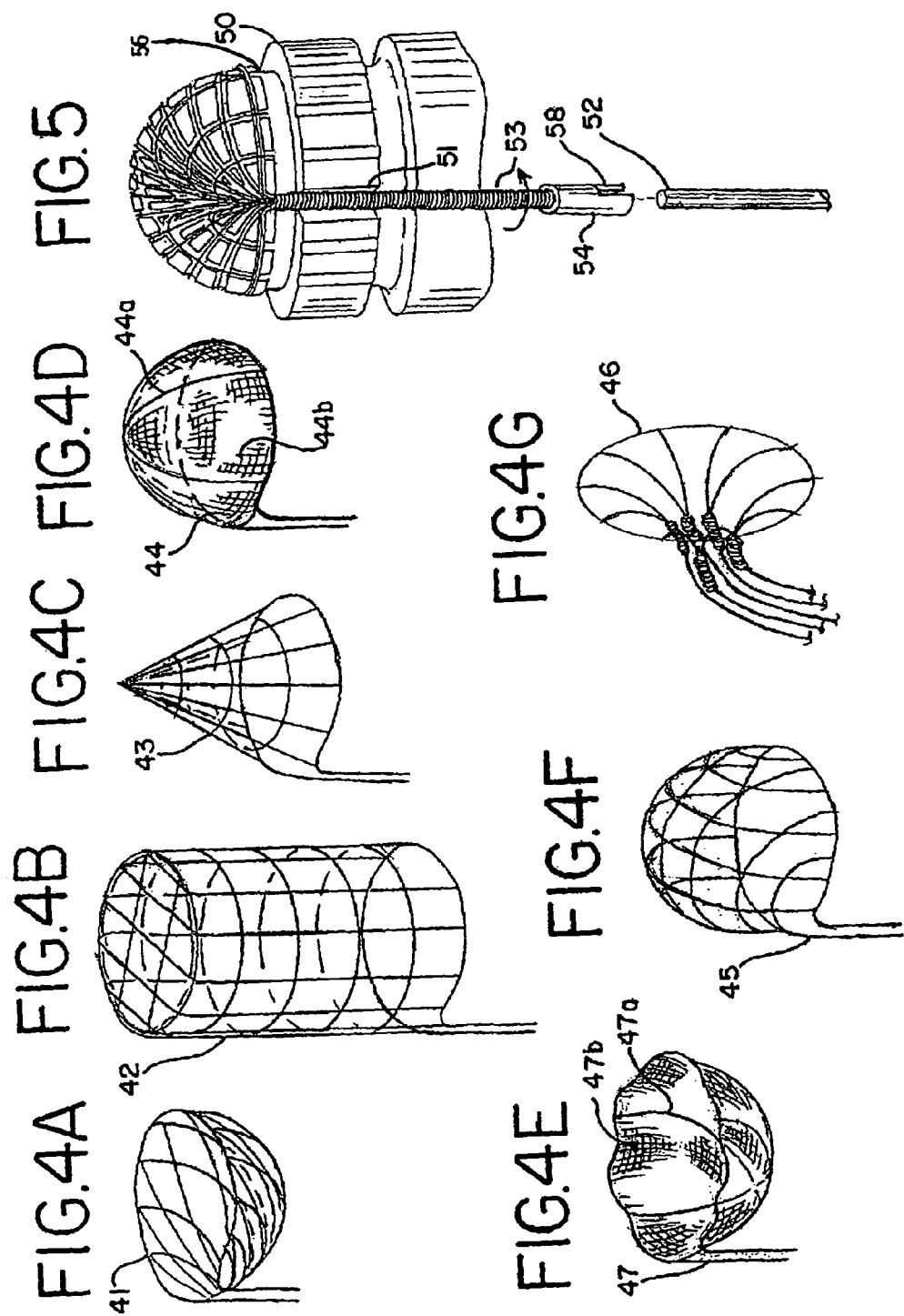

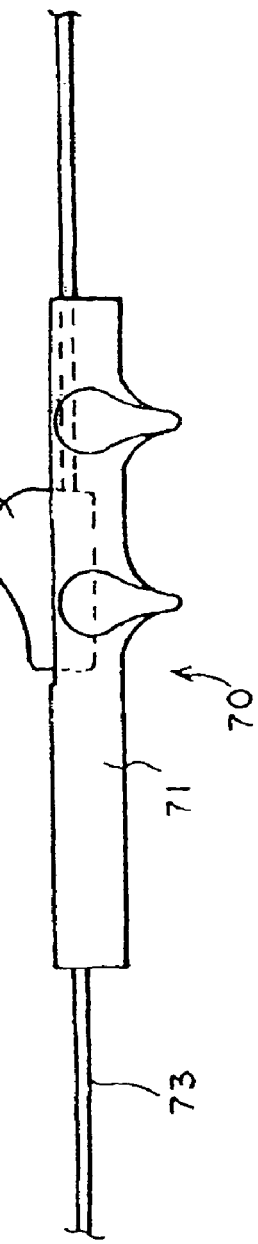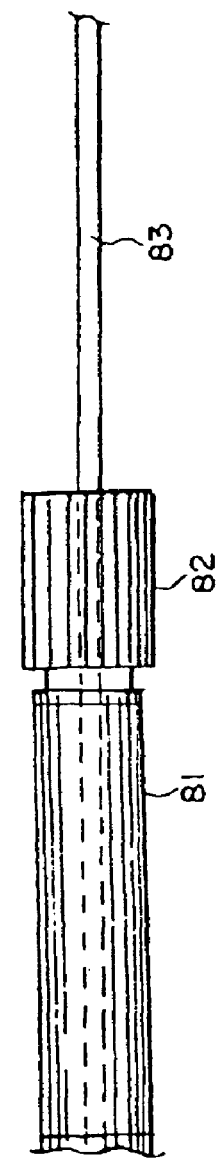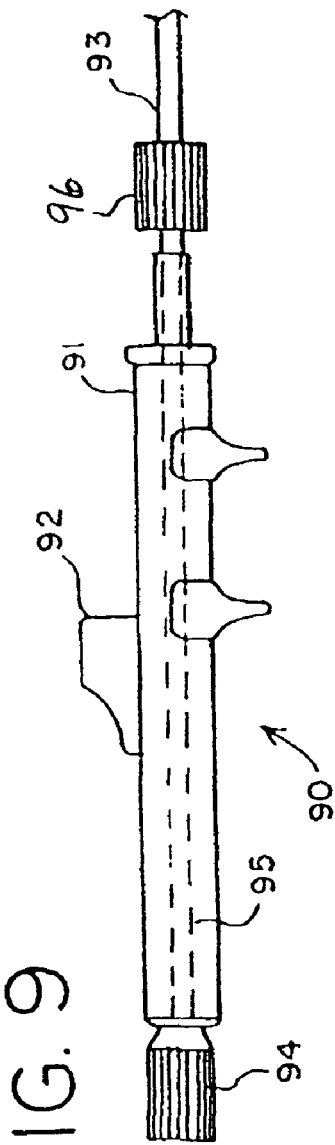

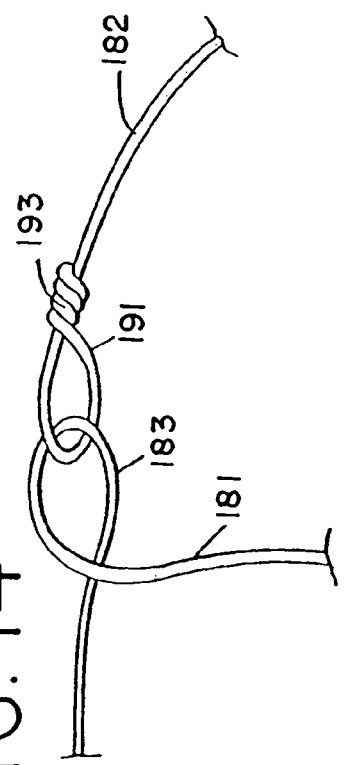
FIG. 14
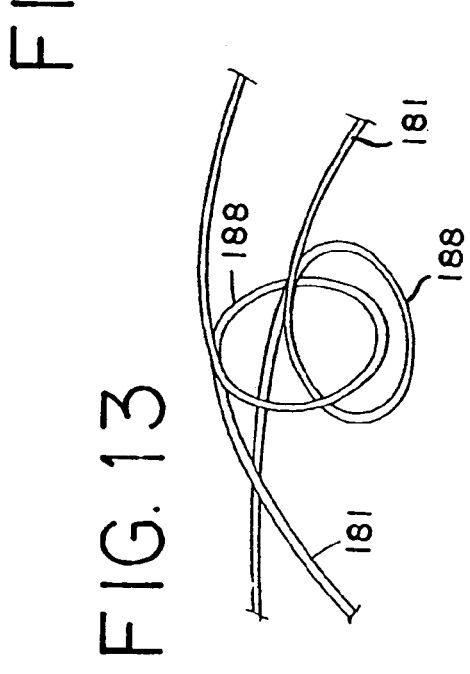
FIG. 13
FIG. 15
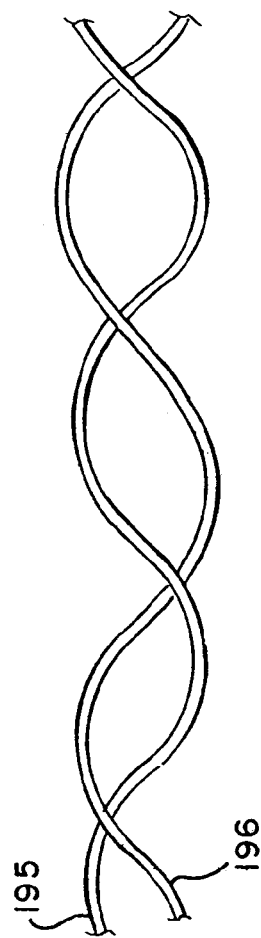
FIG. 16

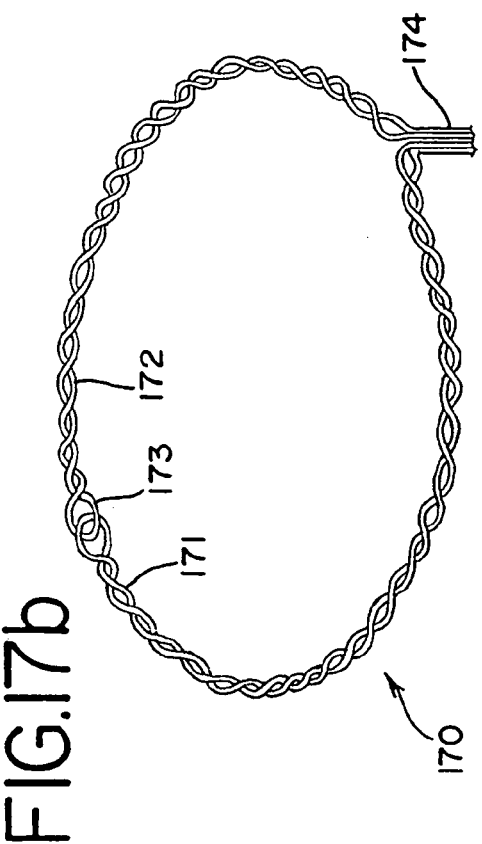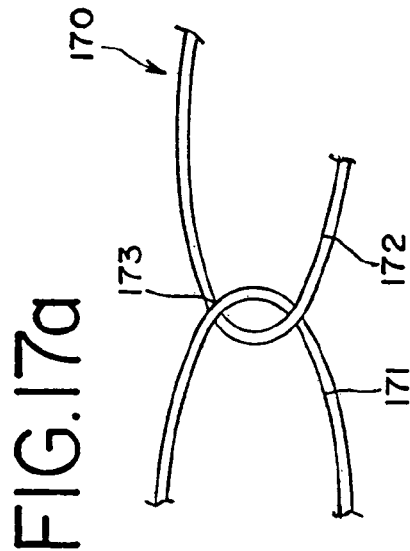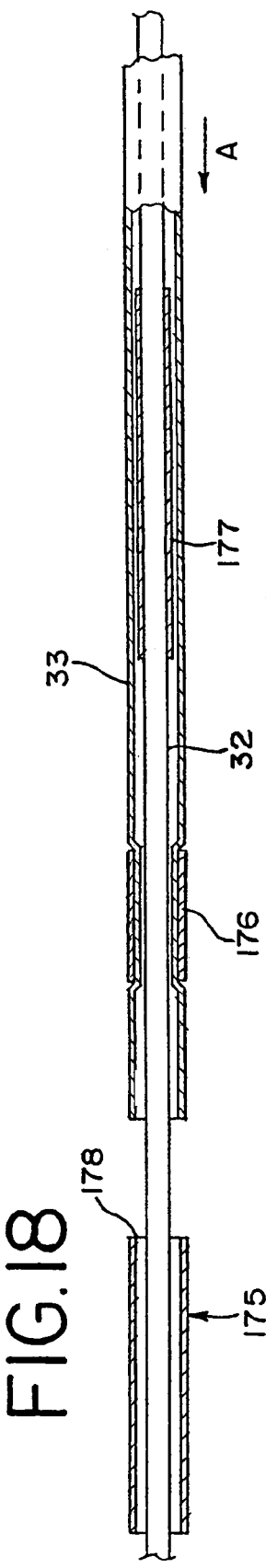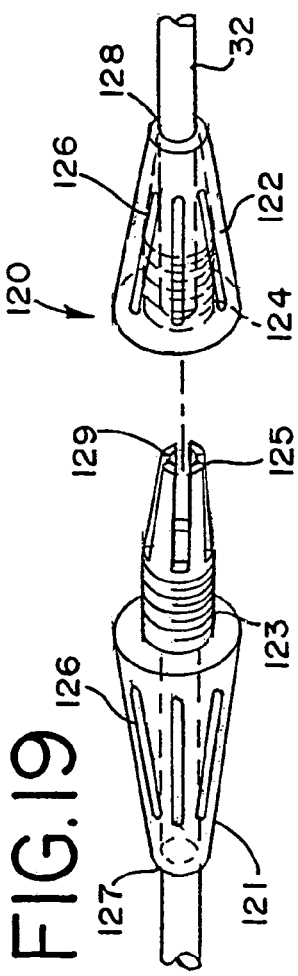
FIG.17a
FIG.17b
FIG.18
FIG.19

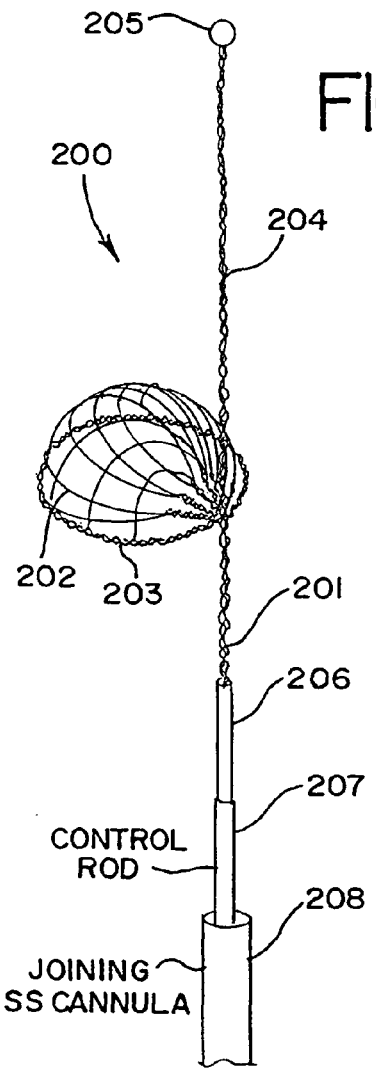
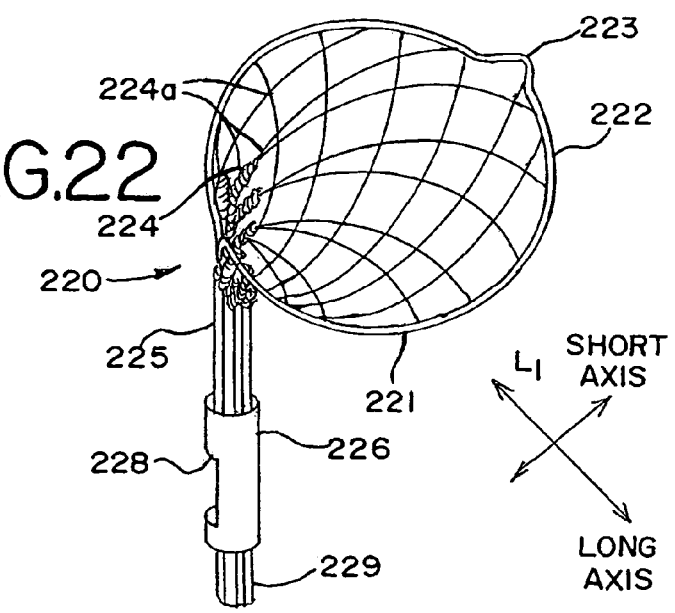
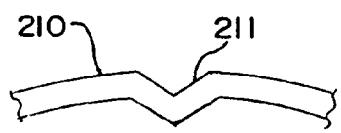
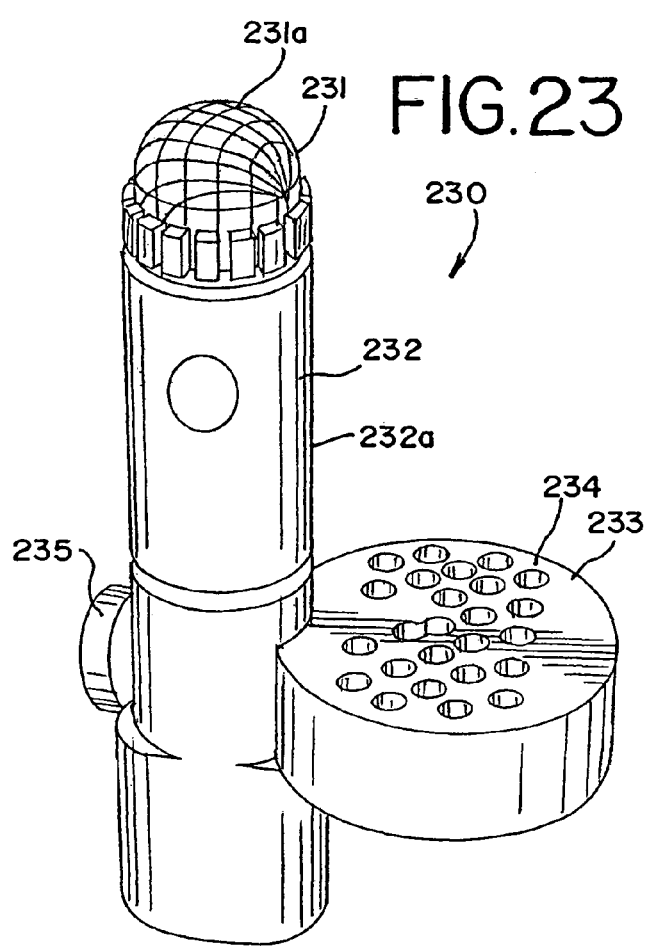

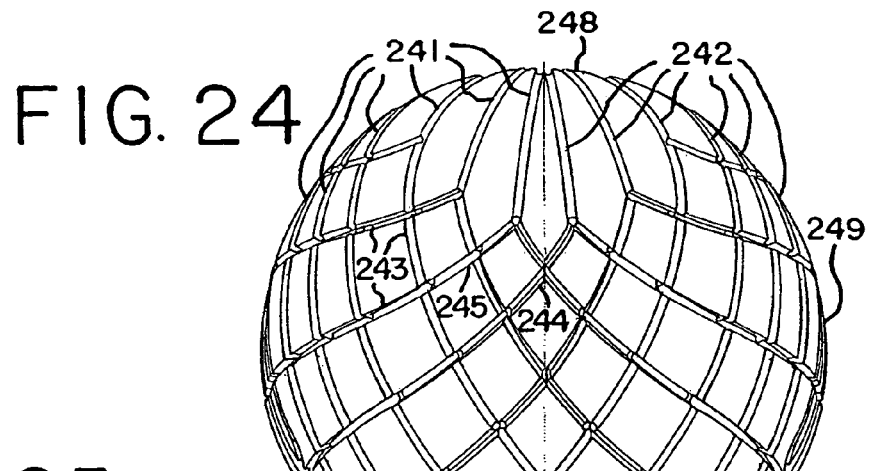
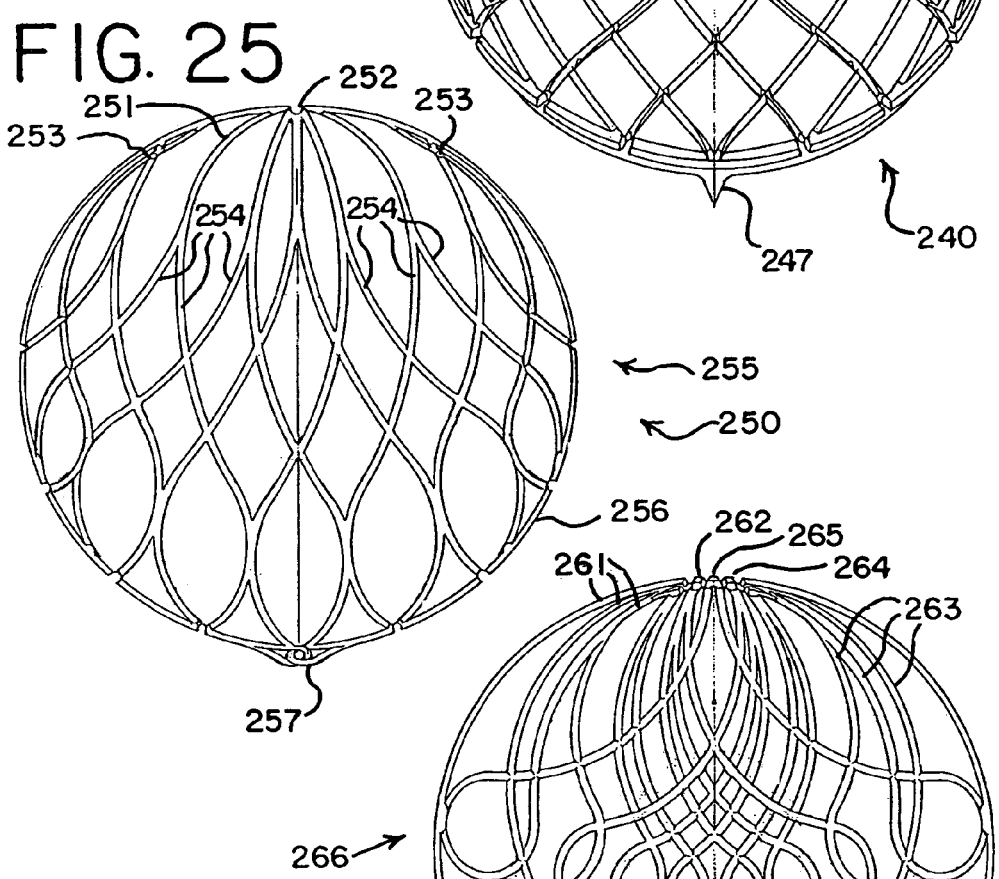
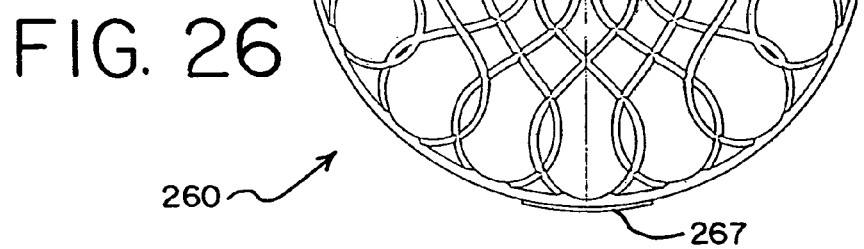

URETERAL BACKSTOP FILTER AND RETRIEVAL DEVICE

This application claims the benefit of the filing date under 35 U.S.C. §119(e) of Provisional U.S. Patent Application Ser. No. 60/491,351, filed on Jul. 31, 2003, which is hereby incorporated by reference in its entirety.

FIELD OF THE INVENTION

The present invention relates particularly to medical devices useful for removing objects from a person, and in particular, for a device useful for removing calculi or fragments from a urinary system and ureter, from a vascular system, or from other body passages. This device also is useful in preventing such fragments from entering the calices of the kidney, or in capturing emboli from vascular systems, and capturing other objects from other parts of the body.

BACKGROUND

Many medical procedures are now available and are being used to remove calculi, stones and the like, which form in body passages, such as kidney stones in kidneys or the ureter, and gallstones in bile ducts. These procedures involve fragmentation or disintegration of the stones, calculi, or other objects by applying energy to them. For instance, kidney stones are typically treated by ultrasonic lithotripsy, electrohydraulic lithotripsy, electro-shock wave lithotripsy (ESWL), laser ablation, laser lithotripsy, and other procedures.

While these procedures are used successfully each year on thousands of patients, some drawbacks remain. For example, when the stones or calculi are fragmented, smaller pieces are formed and must be removed. However, many of these small pieces or fragments may move in undesirable ways because of the retrograde irrigation fluid required for visualization during these procedures. For instance, fragments of a kidney stone may move from the ureter into the kidney or into the calices of the kidney. Many devices are known for anchoring catheters within various body passages or for removing undesirable materials from them. However, these devices generally are not adapted for preventing the migration of fragments from stones, calculi, or other objects within body passages. Such devices are typically not suitable or acceptable for preventing such migration.

It would be useful to have a filter or "catcher" upstream of the stone or calculus, so that after fragmentation, the filter or catcher would capture fragments and prevent them from going upstream or in other undesired directions. For example, ureteral anchors or other catheter anchors, such as a balloon of a Foley catheter could be used to prevent migration, but the balloon is not porous and would not be useful in capturing fragments or calculi after the application or dispersion of energy from an energy source.

A number of devices have been introduced in an attempt to solve this problem. One device is disclosed in WO 98/29043, a ureteral stone occluder having a braided filter. This device has a guide wire and a collapsed mesh or filter at the distal end. The mesh is advanced beyond the stone or calculus and is then expanded before lithotripsy. This device, however, requires sufficient room for the surgeon or technician to advance the filter beyond the occlusion. In another example, U.S. Pat. No. 6,096,053 uses a sheath and a basket, the basket having a number of legs in a generally spiral-shaped net for capturing calculi or stones. However, this device may not be able to move upstream of the device before fragmentation; and the net does not appear to be sufficiently fine for capturing smaller fragments or calculi. U.S. Pat. No. 6,517,550 is directed to a foreign body retrieval device or snare. While this device will likely be able to move upstream of a stone or calculus, it does not appear to be suitable for snaring and capturing small stones or fragments.

What is needed is a device that can overcome the difficulties mentioned above, that is, a device that may be advanced beyond or upstream or downstream of an object or a stone, then expanded or enlarged to effectively block or trap the object or stone. The device will also desirably trap the small particles resulting from lithotripsy or laser operations on the stone or other object. The device will preferably also be easy to collapse and remove from the patient without trauma.

BRIEF SUMMARY

The present invention overcomes these difficulties with a retrieval device that is easy to advance upstream or beyond a stone or calculus, and prevent the downstream flow of fragments or portions thereof away from the surgeon or clinician performing a procedure on a patient. One aspect of the invention is a medical retrieval device. The retrieval device comprises a control rod, and a basket comprising a plurality of loops attached to the control rod, the loops interleaved and formed into an atraumatic periphery of the basket. The retrieval device also comprises a sheath, wherein when the sheath is retracted or the basket is extended, the basket asymmetrically projects in one direction from the sheath.

Another aspect of the invention is a ureteral backstop filter. The ureteral backstop filter includes a control rod further including an attaching portion and a control portion, and a basket further comprising a plurality of loops attached to the control rod, the loops formed interleaved and formed into an atraumatic periphery of the basket, the periphery further comprising a flex point. The ureteral backstop filter also includes a sheath containing the basket, wherein when the sheath is retracted or the basket is extended, the basket projects perpendicularly from the sheath.

Another aspect of the invention is a retrieval device. The retrieval device comprises a control rod and a plurality of superelastic wire loops attached to the control rod, the wire loops formed into a tipless basket with an atraumatic periphery, and a filiform formed from at least a portion of the superelastic wire loops. The device also comprises a sheath, wherein when the sheath is retracted or the loops are extended, the basket projects perpendicularly from the sheath, the loops being in a relaxed condition when outside the sheath.

Another aspect of the invention is a method of making a collapsible retrieval device. The method comprises forming a plurality of loops into a tipless atraumatic basket, in which the loops project from only one side of the basket. The method also includes attaching ends of the loops to a control rod. The method may also include inserting the control rod into a sheath suitable for containing the basket.

Another aspect of the invention is a tool for winding a tipless asymmetric medical retrieval device. The tool includes a basket portion having grooves for placing a plurality of wires for an asymmetric basket, wherein the wires extend from only one side of the basket, wherein at least two wires form an atraumatic periphery of the basket. The tool also includes an axial portion connected to the basket portion, the axial portion extending from the basket portion to a control portion.

There are many ways to practice the present invention, as shown in the following drawings and specification. The embodiments described below are not meant to limit the invention, but rather to describe and illustrate the many ways that the present invention may be used. The advantages of the invention include better control over the removal of fragments, stones, emboli and other objects from the body, as well as better retrieval devices themselves. Embodiments of the present advantage will be seen as leading to easier entry into bodily vessels and lumens, less damage and bleeding, and shorter removal procedures.

BRIEF DESCRIPTION OF THE DRAWINGS

FIGS. 4a-4g depict alternate embodiments of baskets;

FIG. 5 is a perspective view of a tool used to form superelastic materials into the desired shape of a ureteral backstop filter;

FIGS. 7-9 depict alternate handles for using the retrieval device;

FIGS. 10-16 are embodiments of loops for wires forming a basket;

FIGS. 17a-17b depict another embodiment of a loop for a basket;

FIG. 18 is a plan view of a sheath and a control rod with stops;

FIG. 19 is a perspective view of a pin vise type handle useful for controlling embodiments of the ureteral backstop filter and retrieval device;

FIG. 20 depicts an additional embodiment of the invention, including a filiform tip having an atraumatic distal end;

FIGS. 21-22 depict an additional embodiment with an alternative bend point;

FIG. 23 depicts a tool useful for preparing ureteral filters and retrieval devices according to the present invention; and FIGS. 24-30 depict several patterns of windings useful in embodiments of the present invention.

DETAILED DESCRIPTION OF THE DRAWINGS AND THE PRESENTLY PREFERRED EMBODIMENTS

Figure 1:
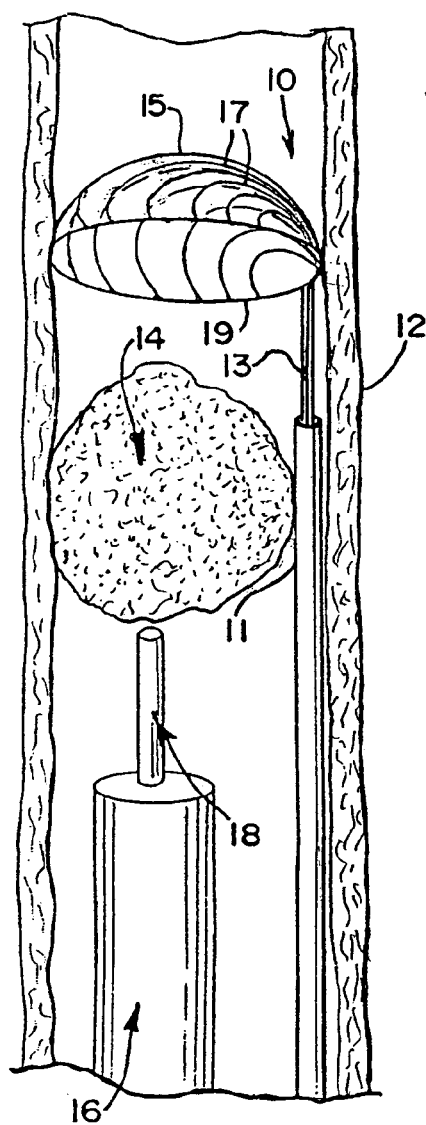
FIG. 1 is a perspective view of a ureteral backstop filter or retrieval device in use with an endoscope and a laser.

Retrieval devices according to the present invention may be used in a variety of applications, in addition to serving as a ureteral backstop. For instance, they may be used in vascular applications, to catch or trap emboli, and in bile ducts to trap or capture gallstones or calculi, in addition to their use in ureters to capture stones and calculi. A typical use is depicted in FIG. 1. A retrieval device 10 according to the present invention is used in a ureter 12 to trap fragments of a kidney stone 14 when they are broken by an endoscope 16 using a holmium laser 18 or other device. Retrieval device 10 is carried in a sheath 11 and controlled by a control rod 13. There is a basket 15 formed from a plurality of loops 17 at the distal end of retrieval device 10. Loops 17 are preferably interlaced or interleaved among each other to for basket 15. The loops may be interlaced or interleaved by simply going over and under each other in a pattern in which the loops or wires will be trained, or they may also be interlaced by means of smaller loops formed in the larger loops, as will be explained below.

When basket 15 is deployed, it will preferably slightly expand the ureter or other body passage and the basket periphery 19 will seal snugly against the walls of ureter or other body passage, to prevent bypassing any objects which are to be removed. If for some reason it is not possible to effect a seal, the retrieval device may be used for retrieval without the sealing function. Periphery 19 is formed from at least one loop or wire, and preferably is joined by additional loops 17 from the remaining of loops in the device.

The basket 15 is contained within the sheath, and the sheath is then advanced through the ureter (or other body passage) beyond or upstream of the calculus or other object which is to be removed. In some applications, the basket is placed upstream of the object sought to be removed, in this case, upstream of a kidney stone stuck in the ureter. In other applications, such as vascular applications, the basket may be placed downstream of an area where emboli or clots are expected, so that the clots or emboli may be captured and removed before the undesirable objects can move downstream.

The sheath may be made of polyimide or other durable, strong material. The sheath may also be made of a composite material, such as a wire mesh (criss-cross wire) reinforcement adding kink-resistance to a polyimide covering. The sheath, containing the basket, is preferably not more than about 2.6 Fr to about 3.4 Fr (0.87 to 1.13 mm) in diameter, although other sheaths and other baskets may also be used. The retrieval device may be deployed by retracting sheath 11 or advancing the control rod 13, causing the basket 15 to emerge from sheath 11. The basket is formed such that when it emerges from the sheath, the basket is held or anchored to the control rod asymmetrically, by only one point or one area on the side of the basket, rather than the basket being centered on the control rod.

In this way, the retrieval device, with the basket still captured within the sheath, may be advanced and held near a wall of the ureter, rather than through the center of the ureter. When the basket emerges from the sheath, the basket tends to deploy in one direction toward one side of the sheath, which should be oriented toward the open ureter rather than the ureter wall. For instance, if position in the ureter is designated according to a clock, and the undeployed retrieval device is advanced through a ureter at about the 12:00 position, the device should be oriented so that the basket expands toward the 6:00 position. In this manner, the basket will deploy and will cover the cross-sectional area of the ureter upstream of the kidney stone or other object, and will seal against the walls of the ureter. It is most advantageous if the bend point or flex point is at about the 6:00 position.

In addition to this asymmetry of the basket, the cross-sectional area of the basket may also possess asymmetry, in the sense that the cross-section is preferably in the shape of an ellipse, rather than a circle. The shorter axis of the ellipse is preferably in the direction between the origin of the wire bundle and a point 180° opposite, while the longer axis of the ellipse is perpendicular to the shorter axis. Asymmetry in the basket or an asymmetrical projection of the basket means that the basket includes asymmetry according to either meaning as discussed above, or according to both meanings.

Figure 2:
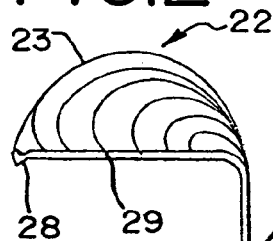
FIG. 2 is a plan view of another embodiment of a retrieval device.

When the laser or other lithotripsy device is used, the kidney stone or other calculus breaks into smaller pieces or fragments. The retrieval device or ureteral backstop filter captures or ensnares these fragments or pieces of the calculus. These pieces are captured and held in the wires which comprise the filter. In one preferred embodiment, as depicted in FIG. 2, the retrieval device 20 comprises a basket or filter 22 made of a plurality of loops of wire 23, interleaved or interlaced to form basket 22. The loops are joined into a cannula or joining portion 24 of a control rod which also has a control portion 25 that may extend to a handle (not shown) for use by a surgeon or technician using the retrieval device. Basket 22 includes a periphery 29 with a flex point 28 for easier collapsing of the basket.

The wires 23 are preferably made of a superelastic or shape memory alloy, such as Nitinol, a nickel-titanium alloy. The wires may also be made from other shape memory metals, such as alloys of Cu—Zn—Al or Cu—Al—Ni. In order to keep the size of the basket and the diameter of the sheath narrow, very thin wires are preferred, such as wires having a diameter of about 0.0025 inches (about 0.063 mm). Round wires are preferred, but wires of any shape may be used, including rectangular wire, square wire, wedge or "pie-shaped" wire, flat wire and triangular wire. Each "wire" depicted in FIGS. 1-3 may in reality comprise two or more wires twisted together for greater stiffness and control of the device.

As is well known in the art, the wires may be formed into a desired shape and heat treated or "trained" into that shape by heating to a certain temperature for a certain length of time. Typically, temperatures in the range of 500-540° C. and times from 1-5 minutes are used. Other temperatures and times may also be used. Shape-memory or superelastic materials are heat treated or annealed from a weak (martinsite) structure to a strong (austenite) structure. The alloys are weak and deformable in the martinsitic state, which is thus useful for forming the basket and the loops. After transformation to the strong or austenitic state, they exhibit a superelastic property so long as the material remains above a transformation temperature, at which temperature it will revert to the martinsitic state. The transformation temperature is desirably a low temperature, well below the temperature of a human body, and preferably below room temperature, which is about 20-25° C. The transformation temperature of the wires and the basket is thus selected to be below the operating temperature of the basket, thus keeping the basket in a superelastic state. In this state, the wires advantageously return to their original, unstressed shape when deforming stresses are removed. The superelastic wire alloy also increasingly resists deformation as the stress load is increased. Thus, when a superelastic basket is collapsed and placed into the sheath, the loops forming the basket are placed into a state of stress. When the loops are deployed, the stresses are removed, and the loops return to the desired shape of a basket.

The baskets are formed by shaping the wires and loops into the desired shape at room temperature or below, preferably with a cold mandrel, and then annealing the properly-shaped basket at the proper annealing temperature for a time sufficient for the transformation to a superelastic state. In one example, a basket is formed from 0.11 mm diameter (about 0.0043 inches) Ni—Ti Nitinol wire and is annealed at 990° F. (about 530° C.) for about 10 minutes. The time and temperature for annealing will vary with the alloy selected and with the diameter (thickness) of the wire. The loops themselves, not merely the annealing oven, must remain at the desired temperature for the proper length of time for the annealing or heat-treatment to be complete. Proper annealing is very important for the wires and the loops to remain kink-free during deployment and operation of the basket. If kinks form for any reason, it may be difficult to deploy (expand) or retract the basket.

The basket is desirably formed before the annealing operation, as discussed above, including all wires or loops in the asymmetric basket. Because of the non-symmetrical shape of the basket, it is possible that it may require more force or more built-in stress in the wires to reliably emerge from the sheath in the desired shape. Therefore, the annealing or heat-treating operation is even more important than normal in building stresses into the wires and the basket.

The retrieval device or basket 22 and the wires are "trained" in the shape of the deployed basket. They are also joined to a joining portion 24 at the distal end of a control rod 25. Control rod 25 may be a solid Nitinol rod or tube, or may be a stainless steel shaft or tube. Nitinol is preferred. The control rod may instead be a number of stranded or non-stranded wires, depending on the degree of flexibility desired. Joining portion 24 may simply be a separate hollow cannula or a hollowed-out portion at the distal end of the control rod or control tube. The wires from the basket are trimmed and joined to the end of the control rod by one or more of several means.

For instance, the wires may be crimped, soldered, or brazed to the control rod, or the wires may be welded. A medically-acceptable adhesive may also be used to secure or join the wires to the control rod. Loctite® 4011 cyanoacrylate has been used for this application and, works well. The wires from the basket may themselves extend to a control handle, rather than using a separate connector and control rod. In one embodiment, the retrieval device comprises 22 loops or wires with 44 ends connected to the control rod. In some embodiments, a separate cannula 24, as shown in FIG. 2, may be used to connect the wires or loops to the control rod 25. The cannula is joined to the control rod, preferably by soldering, although other techniques, such as welding or brazing may also be used. If soldering is used, the control rod is first etched, preferably with acid, followed by neutralizing and drying. Flux is then applied to both the control rod and the cannula, the two are soldered together, and excess solder is removed. Afterwards, the parts should be neutralized, dried and cleaned.

Figure 3:
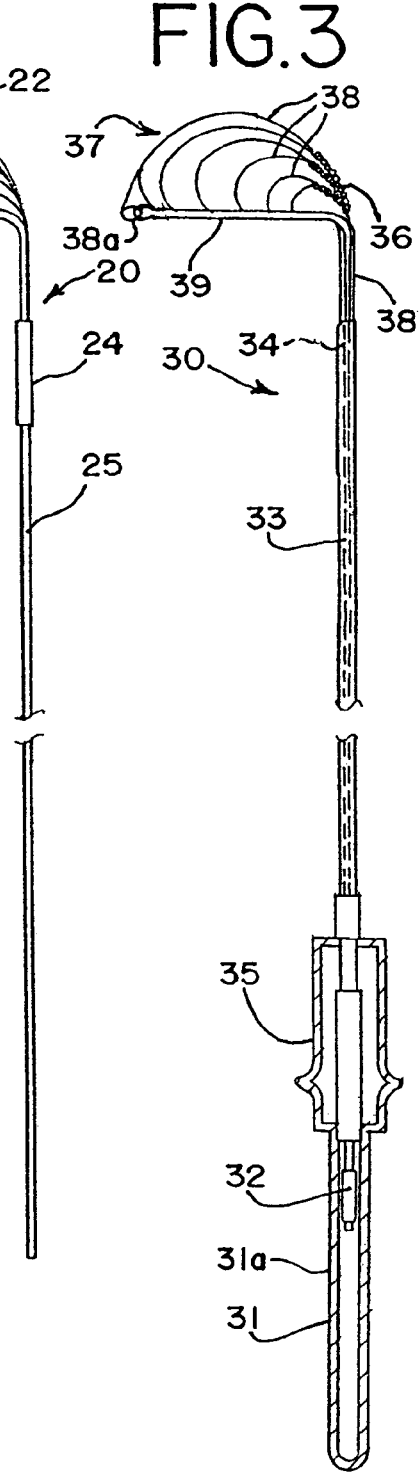
FIG. 3 is third embodiment of a filter or retrieval device.

The retrieval device may also be manufactured with a handle for control. Such a retrieval device with a handle 30 is depicted in FIG. 3. Retrieval device 30 includes a handle 31 with a control rod 32 attached to the handle proximal portion 31a. Control rod 32 has a distal portion 34 for attaching wires 38 forming retrieval portion 37. Wires may leave the bundle of wires in wire pairs 36, the wire pairs twisted together before separating into single wires 38 for attachment to the periphery 39. The wires may be in groups of three or more, but wire pairs are preferred. The wires form a better net when they are separated into individual wires as shown in FIG. 3.

The periphery 39 may be formed from two wires 39 linked at point 38a and twisted. Link point 38a is also a flex point for the basket, allowing the user to more readily open and close the basket. The handle may include a control lever 35 for retracting a sheath 33. Alternatively, sheath 33 may be affixed to the handle 31 and control lever 35 may attach to control rod 32 for pushing retrieval device 38 from the sheath, thus deploying the retrieval device. Portions of the device 30 in which the wires are cut or which could possible cause trauma may be covered with a protective material, such as shrink tape or a shrink tube (not shown) over the distal portion of control rod 32.

It is very important for the retrieval device to cause as little trauma as possible to the ureter, or other body area where the retrieval device is employed. For instance, if a kidney stone is fragmented, it may require many trips in and out of the ureter, to remove the many fragments created. With each further fragmentation of the stone, the passage beyond the stone is easier to traverse, but with each passage, there is more and more danger of trauma to the patient. Even if a ureteral sheath is used, the chance of trauma to nearby organs or areas of the body increases with each trip. It is therefore very important that the retrieval device, and especially the basket itself, be as smooth and atraumatic as possible.

The basket is formed as described above, and a periphery 39 of the basket may be formed from the two linked and twisted wires as described above, the periphery then joined by all or most of the remaining wires 38 being twisted into the periphery. The periphery of the basket is the outer portion of the basket where the wires abut the body vessel, such as a ureter, or a urethral sheath or other passage, and form at least a partial seal against the wall thereof. As the construction has been described, it is reasonable that the periphery be inherently atraumatic, or at least have a high degree of smoothness. The wires that constitute the basket and the periphery do not begin or end in the basket itself, but rather in the joint in the distal end of the control rod. In addition, the joint itself may be smoothed or may be covered with shrink tubing. Therefore, no sharp edges, no ends, no cuts, and no abrasive portions exist within at least the portion of the basket that contacts the patient.

In addition to the concave hemisphere (from the viewpoint of the surgeon or clinician) shape of the basket, other shapes are also possible, as depicted in FIGS. 4a-4g. These shapes include a convex hemisphere 41, a three-dimensional cylinder 42, a cone 43, a reverse-umbrella 44, a sphere 45, an umbrella or saucer shape 46, and an irregular shape 47. Each of these shapes has four essential characteristics: each is atraumatic, or non-injurious to the patient; each is capable of having a periphery or sealing portion that seals against a ureter or other bodily vessel or cavity; each may be formed from a plurality of wires or loops, or at least from one loop and a mesh net, to capture fragments, calculi, emboli, or other objects which are to be removed from the body; and each is capable of being formed in an asymmetric manner such that the ends of the loops project from only a point or a single area on the periphery of the device.

The embodiments of FIGS. 4d and 4e, in addition to the wire basket, also use a filter mesh to capture objects that are desired to be removed. In FIG. 4d, a reverse-umbrella shaped basket 44 comprises one or more wire loops 44a and a filter mesh 44b. The filter material may be any mesh or filter material desired. For vascular applications, the filter shown be blood-permeable, while retaining clots, thrombi and emboli. Sacs or filters woven from thin, bio-compatible materials will work well, if they have openings or pores in a range of about 20 to 400 micrometers in diameter, preferably about 80 micrometers in diameter. The pore size will be a function of the number of warp threads, the number of weft threads, the pattern, and the tightness of the weave. Materials may include, but are not limited to, polyester, polyethylene, polypropylene, polyurethane, polyethylene terephthalate, nylon, and PTFE. Composites of these materials may also be used.

In another embodiment, depicted in FIG. 4e, the basket 47 is an irregular shape, including at least one wire loop 47a and a filter mesh 47b. Other shapes may also be used. In nonvascular applications, the mesh may be may looser than mesh 44b described above. In some applications, the mesh may be made of the polymeric materials described above, but in which the mesh openings may be from about 0.013 to about 0.050 mm (about 0.0005 to about 0.002 inches) across. Other meshes and other openings may also be used.

The basket may be formed from a plurality of wires 53 with a forming tool 50 as shown in FIG. 5. As shown in the figure, the wires meet or join at a single point or area 51 of the tool. Since the wires each must have finite thickness, and since at least one or two wires or loops are required to form the simplest basket, it is not physically possible to have all the wires meet or join at a single point on the periphery of the retrieval device. Therefore, it is appropriate to speak of a single area, rather than a single point, where all the wires meet, forming a wire bundle, before being joined in a connector or control rod. This point or area is necessarily on the periphery or edge of the basket described above. Since most embodiments may have a roughly circular or elliptical cross-section, it may be better to state a range for the portion of the periphery where the wires are gathered, such as from 0° to about 30°.

For instance, when one embodiment of the basket or retrieval device is deployed, the wires extend from the control rod or connector to the periphery of the basket, and the wires form an interface of about 10° on the periphery of the basket. Other embodiments may use a lesser portion or a greater portion of the periphery. When the word "point" is used in conjunction with the gathering of wires on the periphery to lead to the connector or control rod, the word "point" is used in the sense of a narrowly localized place or area.

All the wires 53 are then joined at this point and the wires are then routed to the control rod or to a connector 54 for joining to a control rod 52 as described previously. Connector 54 may have a notch 58 for better processing, such as to encourage solder flow and complete filling of the connector. The basket may be formed from as few or as many loops as possible. A basket may be made with one loop, such as for a basket using a filter mesh. At present, baskets with 22 loops having 44 ends have proved useful. More or fewer loops than 22 may also be used. The periphery 56 is formed by intertwining the appropriate portions of the wires 53 during the forming process as desired. This operation is preferably carried out at a cold temperature, preferably below room temperature. The bundle of wires is also preferably twisted, as shown by the arrow in FIG. 5, to stiffen the wire bundle between the basket portion or periphery 56 and connector 54. This twisting stiffens the wire bundle and makes it easier for the physician to control the maneuvering of the finished filter basket or retrieval device.

Connector 54 is preferably radiopaque so that it may easily be seen with x-rays or other imaging techniques. One way to accomplish this is to use stainless steel connectors. Because Nitinol is not highly radiopaque, at least one component for the backstop filter or retrieval device may be made with a radiopaque marker, such as embedded gold, tungsten, stainless steel, tantalum or platinum threads or cores. The connector may also be made radiopaque by crimping platinum or other radiopaque metal on the outer portion of the connector. Alternatively, one or more components may be echogenic by dimpling or other techniques well known to those skilled in the art, as shown in U.S. Pat. No. 5,201,314, the contents of which are hereby incorporated by reference.

It has been found that the retrieval device or ureteral filter basket according to the present invention is more readily extended into a body vessel, and more readily collapsed into the sheath, if the device possesses some asymmetry. In particular, it is advantageous if the tool from which the device is made is not "circular" in cross section, or "spherical," but rather, has an aspect ratio. That is, if a sphere, or a circular cross-section, may be considered to have two major axes of equal diameter, a tool to make filter baskets and retrieval devices according to the present invention preferably has an elliptical shape, in a three dimensional object. The major and minor axes preferably have aspect ratios from about 50/50 to about 60/40, and more preferably from about 55/45 to about 60/40. As shown in FIG. 4G, the shorter axis is the axis from the area where the wires join to 180° on the other side; the longer axis is perpendicular to the shorter axis.

When the wires are arranged on the tool as desired for the final configuration of the basket, the tool and the wires are heat-treated or annealed as described above, with the wires and tool subjected to the desired temperature for the amount of time necessary to insure the desired degree of elasticity and "spring-back" so that the basket will easily assume the desired shape when the surgeon or clinician extends the basket or retracts the sheath. The basket may be in the shape shown, in the shape of a concave hemisphere, from the viewpoint of the surgeon.

Figure 6:
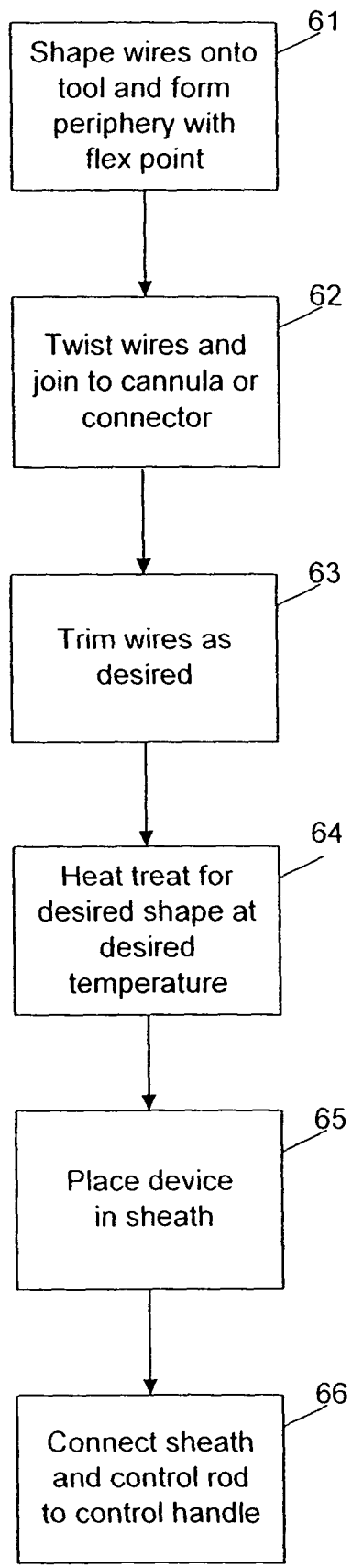
FIG. 6 is a flowchart for a method of forming a retrieval device.

A flowchart depicting a process for forming a retrieval device according to the present invention is depicted in FIG. 6. A first step 61 of the process is to cut and shape the wire loops, preferably Nitinol wires, onto a forming tool and to form a periphery or edge of the basket, the periphery having a flex or bend point. The user should make sure there are no burrs or sharp edges aside from the ends of the wire loops. As shown in FIG. 5, the loops are gathered at one point on the periphery of the basket and then led to a connector or control rod for attachment later. The wires are draped over the hemispherical (or other shape) grooved tool and wound to form a retrieval basket and a seal 39 (show in FIG. 3). Formation preferably takes place at a cold temperature, well below room temperature. The next step 62 is to twist the wires and join the wires to a cannula or other connector. The wires may then be trimmed 63 as desired.

The formed device is then heat treated into the desired shape by keeping the loops or basket in the desired shape for a sufficient time at a sufficient temperature, according to heat-treat schedules for the alloy used. After heat treat come assembly steps. The retrieval device is then assembled by placing 64 the formed loops or basket into a sheath and connecting 65 the sheath and the control rod to a control handle. The device is then ready for any testing, cleaning, and packaging desired.

Handles other than the control handle depicted in FIG. 3 may also be used with the retrieval device or backstop filter. Additional handles are depicted in FIGS. 7-9. FIG. 7 depicts a sliding taper clamping handle 70, having a housing or body 71 and a moving wedge or taper portion 72. In this handle, the taper portion 72 is used to fix the position of the control rod 73 for the retrieval device, the control rod depicted as extending through the handle. The sheath may be controlled by hand or by another handle or device. If desired, clamping handle 70 may be used to fix the position of the sheath, while the control rod is then manipulated by hand or by another handle or device.

FIG. 8 depicts a pin vise 80, which may be used alone or in combination with another pin vise or other control mechanism to operate a retrieval device or ureteral backstop filter. Pin vise 80 includes a handle 81 and a collet 82, the collet used to secure control rod 83 to the pin vise. A second pin vise or other handle may be used to control the sheath. Alternately, the pin vise used to control the sheath and the control rod manipulated by hand or another device.

It is preferred that the handle be removable from the backstop filter or retrieval device during the procedure itself. For instance, an endoscope may be used to place the filter, but the endoscope is also needed to place a lithotripter, such as the holmium laser mentioned for fragmenting the calculus. Thus, after the backstop filter is placed, the handle of the device is removed and the endoscope is also removed, leaving the device within the patient. The endoscope with the lithotripter is then reintroduced, and the handle of the backstop filter or retrieval device is reassembled. Thus, the removable handle allows parallel placement of the endoscope and the device within the patient. In order to better allow the removal and re-placement of the device, it is preferred that the retrieval device be a little longer that normal, i.e., about 115 cm for normal length and an additional 30 cm of control rod extending from the proximal end of the sheath, for a total length of about 145 cm (57 inches) from proximal end to distal end of the basket, as measured in the collapsed position in the sheath.

FIG. 9 depicts a coaxial movement handle for controlling both the sheath and the control rod. Coaxial movement handle 90 includes a body 91 and a control lever 92. There is a forward clamp 96 for removably clamping sheath 93. There is a rearward clamp 94 for removably clamping control rod 95. The control rod, and therefore the basket, may be extended by pushing the control lever forward. In other embodiments, the control rod may be attached to the forward clamp with the sheath attached to the rearward clamp, the sheath extended or retracted with the control handle. In some embodiments, the sheath may have a flared end, and thus may be permanently connected to the handle. Any other handles useful for controlling the control rod or the sheath, or both, may be used instead. Embodiments of the invention are not limited to the handles shown.

Figure 11:
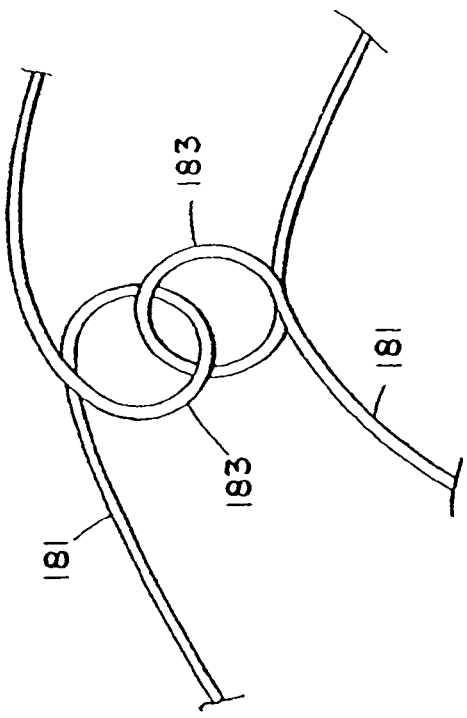
Figure 10:
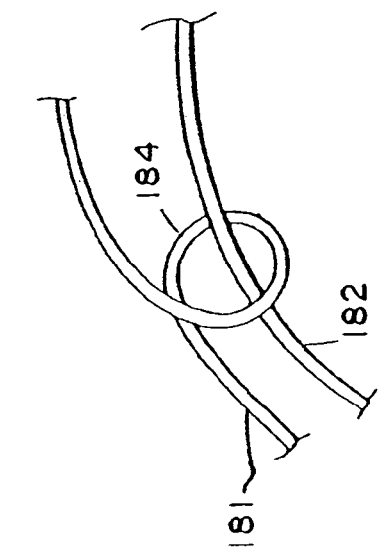

FIGS. 10-15 depict several embodiments of small loops that may be used to interlace or interleave the wires, large loops, and legs that form the basket. In FIG. 10, a basket is formed from two large loops 181, 182, wherein large loop 181 is formed with an integral small loop 184 that encircles the other large loop 182. The diameter of the small loop is desirably formed as small as possible without kinking. FIG. 11 depicts a basket formed from two wires 181, each formed with a small loop 183 that encircles the other small loop. In both FIGS. 10 and 11, the small loops will coincide with the outer portion of the basket.

Figure 12:
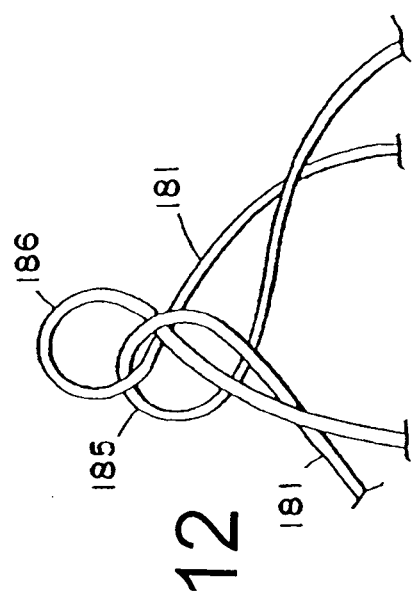

In FIG. 12, a first wire 181 is formed with a small loop 185 and a second wire 181 is formed with a small loop 186, the small loops intertwined with the wires in such a manner that the loops are external to the basket, that is, the small loops depend outwardly from at least one of the large loops. This is not a preferred embodiment, because the small loops desirably are formed inside the basket, and thus preferably depend inwardly from the large loops. Such a desirable configuration is depicted in FIG. 8. In this preferred embodiment, a first wire 181 is formed with a small loop 188 and a second wire 181 is also formed with a small loop 188. The small loops intertwine as shown, and will be contained within the basket, i.e., the small loops will depend inwardly from the large loops.

The embodiments of FIGS. 10-13 have used large-loop wires, in which a wire starts at the inner cannula with one end, forms part of a basket at its middle, and terminates at the inner cannula with the other end of the wire. Other embodiments of the basket may use a single "leg," in which a wire starts at the inner cannula at one end, and then terminates at the basket, as shown in FIGS. 14-15. In FIG. 14, a large loop of wire 181 is formed with a small loop 183, while a wire leg 187 terminates with a small loop 191, the small loops 183, 191 intertwining and acting to restrict movement of both the wire loop 181 and the leg 187. In both FIGS. 14 and 15, leg 187 should be terminated back upon itself in a joint 193, 194 that has no sharp edges or burrs. This will ensure that the basket and the extractor will remain atraumatic. As mentioned above, it will be understood that the wires of the basket may also be trained for over-and-under placement as another technique for interleaving the wires and forming a basket.

Wires used for the periphery 56, or peripheral wires, may begin with a single wire with a bend or deformation at 180° from the area where the wires gather, such as shown in FIG. 5. In one alternate embodiment, the periphery of the basket may begin with two or more wires, preferably twisted together. This embodiment is depicted in FIG. 16, in which two wires 195, 196 are looped together multiple times in forming the periphery of the basket. The loops may be formed by simply twisting the wires together the desired number of turns and then placing on the forming tool 50. Each twist of the wires creates a small loop further joining the two wires within the large loop formed by the two wires around the periphery. More than two wires may instead be used.

The peripheral loop 170 may be made of two wire loops linked and twisted, as shown in FIGS. 17a-17b. Single wire loops 171, 172 may be joined at joint 173 and twisted as they are brought back to wire junction or flex point 174, at which point the ends of wires 171, 172 and joined with all other wire loops forming a basket. The loops may then be brought together into a cannula which is joined to a control rod, as shown in FIG. 2. Other control configurations may also be used. Other wires forming the basket may also be used in pairs, with wires twisted separately and preferably joined to the peripheral wires away from the wire junction. Instead of pairs, three wires may be used, or even more, but pairs are preferred.

It has been found advantageous to provide stops on the device in order to limit the travel of the control rod with respect to the sheath, or vice-versa, to limit the travel of the sheath with respect to the control rod. For instance, in some embodiments, the loops or the control rod need only traverse about 1 cm to 3 cm in order to deploy the basket from the sheath. Placing travel stops or limits on the device makes it easier for a physician to deploy the basket and thus use the device. FIG. 18 shows one embodiment of a ureteral backstop filter and retrieval device in which travel is limited. Portions of control rod 32 with a ureteral backstop filter and retrieval device at its distal end (to the right in FIG. 8, not shown) are within sheath 33. Heat-shrink tubing 177 may applied to control rod 32 for ease of movement. Cannula 175 is applied to control rod 32 and cannula 176 is applied to the outer surface of sheath 33. The cannulae act as stops in the travel of the control rod or the sheath with respect to one another. Cannula 175 may be applied to control rod 32 with a layer of film or plastic in-between the cannula and the control rod.

In this embodiment, the stops work as follows. The basket is normally closed or retracted into the sheath. A user grasps control rod 32 with a handle (to left in FIG. 18, not shown) and grasps sheath 33 with a handle or with his or her hand. Sheath 33 is retracted by pulling it to the left, in the direction of arrow A. Travel of sheath 33 is limited by the distance sheath 33 and cannula 176 can travel to the left, which is limited by the interference with cannula 175 and control rod 32. Travel of sheath 33 to the right may be limited by interference with heat-shrink tubing 177, which acts as a stop.

An additional handle which is useful in operating embodiments of the invention, such as described in FIG. 18, include a pin vise/collet style handle. One such handle is depicted in FIG. 19. Collet style handle 120 has male and female portions 121, 122, each with a central bore for a control rod and each portion tapered, narrowing towards the end of the handle. Both portions 121, 122 have grooves 126 on the outer surface for easier gripping by a user. Male portion 121 has external threads 123 and collet-style fingers 125 for gripping a control rod. There is a passage for the control rod defined by distal orifice 125 and central bore 127. Female portion 122 has female threads 124 and a tapered central bore 128 for compressing fingers 125 to grip wire control rod 32. This collet-style handle or gripper may be used for retrieval devices or may also be used for other medical applications, such as for maneuvering or torquing wire guides.

In some applications of the present filter and retrieval device, it may be useful to include what is generally known as a filiform tip at the distal end, to better enable the physician to control the maneuvering of the device beyond a stone or other obstacle in a body passage. FIG. 20 depicts a ureteral backstop filter and retrieval device 200 having a filiform tip 204 with an atraumatic distal end 205. Device 200 is made from a plurality of wires 201. Device 200 includes a filter 202 made from a plurality of wires including at least two wires which form a periphery 203 of the basket, preferably by being twisted together. At least two wires 201 may be twisted or braided together to form filiform tip 204. The wires may be terminated at distal end 205 by forming their distal ends into a solder ball or other smooth, atraumatic surface or feature. Filiform tip 204 may include the same number of wires throughout its length, with uniform stiffness. Alternatively, tip 204 may be tapered throughout its length, with fewer wires at the distal end than at the proximal end of the filiform. Each wire should terminate in an atraumatic fashion, such as by being secured to the other wires at a smooth joint.

In forming the filiform tip, the wires which are used in filiform 204 preferably begin at cannula 206 and are wound on tool 50 (FIG. 5) or a similar tool, to form part of filter 202. The wires are then brought out to the filiform 204 rather than being routed to cannula 206. The distal end of filiform 204 is then made atraumatic to minimize any tissue damage to the patient. As discussed above in other embodiments, the wires may be joined at a cannula 206, preferably made of stainless steel or other radiopaque material. The opposite end of cannula 206 is joined to a control rod 207. Deployment of the device is controlled by sheath 208. In at least one embodiment, filiform 204 and tip 205 remain outside sheath 208 even when filter 202 is collapsed inside sheath 208; in other embodiments, filiform 204 and tip 205 may be completely retracted into sheath 208 as desired. In embodiments having a filiform, the retrieval device has two distal ends, the filiform being at the distal end of the device, while the basket also has a distal bend point, the bend point of a peripheral loop or the joining portion of two wires twisted together at a bend point.

In some embodiments, it may be desired that other portions of the filter or retrieval device be radiopaque. Radiopacity may be added by incorporating wires made of tungsten, gold, tantalum, stainless steel or platinum, or other radiopaque materials, in portions of the device or the basket as desired. For example, one or more wires which form the periphery of the basket and are then routed to form the filiform may be radiopaque. In other embodiments, a few wires or radiopaque wires may be routed directly from cannula 206 into filiform 204, without first being routed through the basket portions of filter 202. Radiopacity may also be added by selectively adding a radiopaque marker or piece of radiopaque metal precisely where desired in the device. The metal may be in the form of a foil or a wire, and may be added by crimping, soldering, adhering, or any other suitable technique.

Retrieval devices and filter baskets according to the present invention may also be made by at least one other method using a bend point or flexural point, as shown in FIG. 21. A peripheral wire 210 may be bent or shaped with a "beak" 211 or undulation. This bend provides a basket made with this peripheral wire with an interruption in the flexural modulus of the periphery, allowing the basket to more readily "bend" so that it may be collapsed or folded into a sheath. The bend preferably is gentle so that it does not subject the basket to fatigue, nor does it cause trauma to the patient. However, the bend is sharp enough so that the user can readily collapse and retrieve the basket as desired. In one embodiment, the wire is about 0.11 mm (about 0.0043 inches) diameter, and is bent or deformed symmetrically as shown about 1 mm (about 0.039 inches) out of plane. More or less bending is acceptable, so long as the user may easily collapse and extend the basket. Nitinol wires are preferred for these loops.

FIG. 22 depicts an embodiment of a retrieval device with a "beak" in its peripheral wire. Retrieval device 220 includes a basket 221 formed from a single peripheral wire 222 having a bend or beak 223 about 180° away from the wire bundle 225 at which the wires of the basket meet. The basket also preferably includes wire pairs 224 which are formed as twisted pairs for a portion of their travel to the periphery, but in which the individual wires 224a split away from wire pairs 224 before themselves being twisted into, and becoming part of, the periphery of the basket. Most, if not all, of the wires meet in wire bundle 225 and are twisted before being secured to cannula 226. Cannula 226 may have a notch 228, such as a notch to encourage solder flow, for better joining of wires to the cannula, and for joining cannula 228 to control rod 229.

Basket 221 may have asymmetry, in which the width of the basket has a longer axis, as shown, and the length of the basket is somewhat shorter and has a shorter axis, as shown. In one embodiment, the basket may be made with a slight asymmetry, as described above, such as a 55/45 ratio of the major axis of the cross-section to the minor axis. In this embodiment, the asymmetry is lost when the basket is retracted into the sheath and collapsed. The elastic deformation of collapsing the basket leads to a slight plastic deformation, and the cross-section then assumes a circular shape, while basket becomes hemispherical.

There are many ways to practice the invention. One of the useful features of embodiments of the invention is the ability of the basket to emerge from only one side or one point of the sheath, instead of emerging from and spreading out 360° from the sheath. With embodiments of the present invention, 360° coverage and sealing of the lumen is accomplished, but the basket or filter spreads from only one side or one point of the basket. The basket may also include additional loops or wires from one point to another in the basket, so long as all the loops emerge from the same point or area of the sheath. With this advantage, a surgeon does not need to place the sheath in the center of the lumen, but as shown in FIG. 1, a sheath of the retrieval device may be on the periphery of the lumen and the basket or filter can still fill and seal the body lumen. Note that when the wires are routed to a single "point" or "area" during manufacturing as shown in FIG. 5, the basket necessarily emerges from only one "side" of the basket, as the wires emerge from only one point or area.

A tool useful for making ureteral backstop filters and retrieval devices is depicted in FIG. 23. The tool is preferably made of brass or titanium. Tool 230 includes a basket portion 231, with channels or grooves 231a to accommodate the wires used for the basket. The grooves preferably accommodate a single peripheral wire having a beak or flex point on the side opposite control-rod side. Alternatively, the grooves may instead accommodate a peripheral wire that includes two wires linked together and twisted. The axial portion 232 has an axial channel 232a to accommodate the wire bundle from the loops and wires forming the basket. The axial portion also has a winding tool 233 with apertures 234 for the wires or wire pairs. Winding tool 233 may be secured to tool 230 via securing screw 235.

In addition to the embodiments described above, other embodiments or patterns of winding the wires or loops to form a basket are also possible. A few alternate embodiments are depicted in FIGS. 24-28. FIG. 24 depicts a top view of a winding pattern useful for a basket 240 for embodiments of the retrieval device. In this embodiment, about 12 pairs of wire or loops are shown, six pairs 241 on the left and 6 pairs 242 on the right. The pairs originate in the vicinity of the control rod side 248, and the individual wires 243 leave the pairs and interleave and interlace at junctions 244, 245, until they arrive at the periphery 249. The periphery may have a flex point, such as beak or bend 247, located at about 180° from the control rod vicinity.

Another top view of a pattern is depicted in FIG. 25, in which a plurality of pairs 251 or triples 253 of wires emerge from the vicinity 252 of the control rod. The pairs or triples then split into individual wires 254 and interleave into an intricate pattern 255 before joining periphery 256. Periphery 256 may include a joint 257 formed from two wires joined and twisted together, as described above for FIGS. 17a-17b. Yet another top view of a pattern is depicted in FIG. 26, in which basket 260 is formed from about 18 wire groupings. The wire groupings include 6 pairs 261, 263 of wires and 2 triples, 262, 264. The wire groups emerge from the vicinity 265 of the control rod before splitting into individual wires and interleaving to form the intricate pattern 266. The wires rejoin to form periphery 267.

Figure 27:
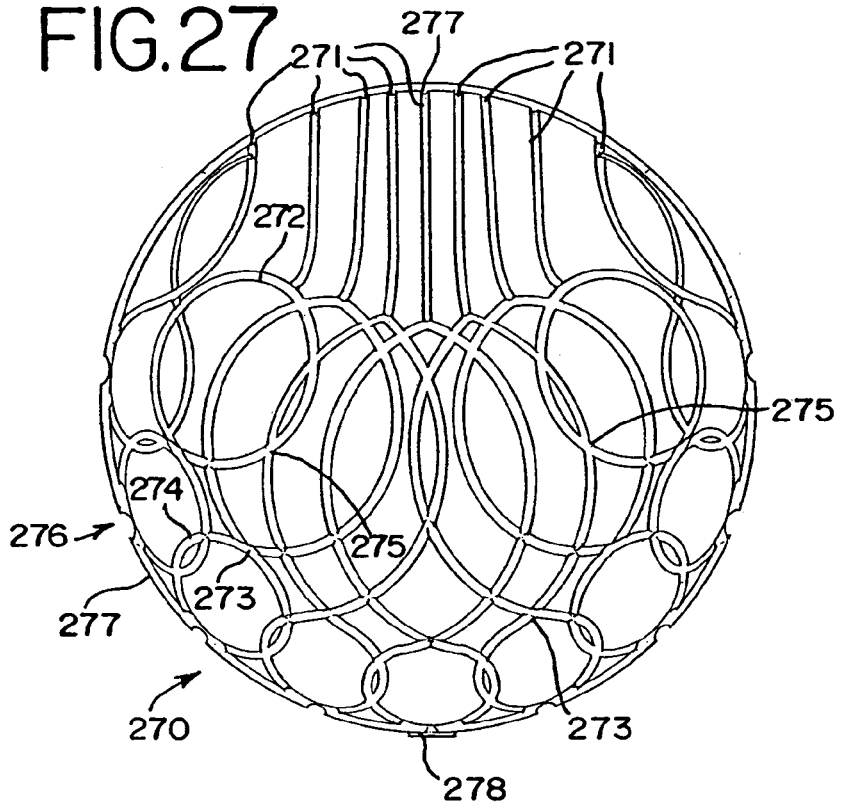
Figure 28:
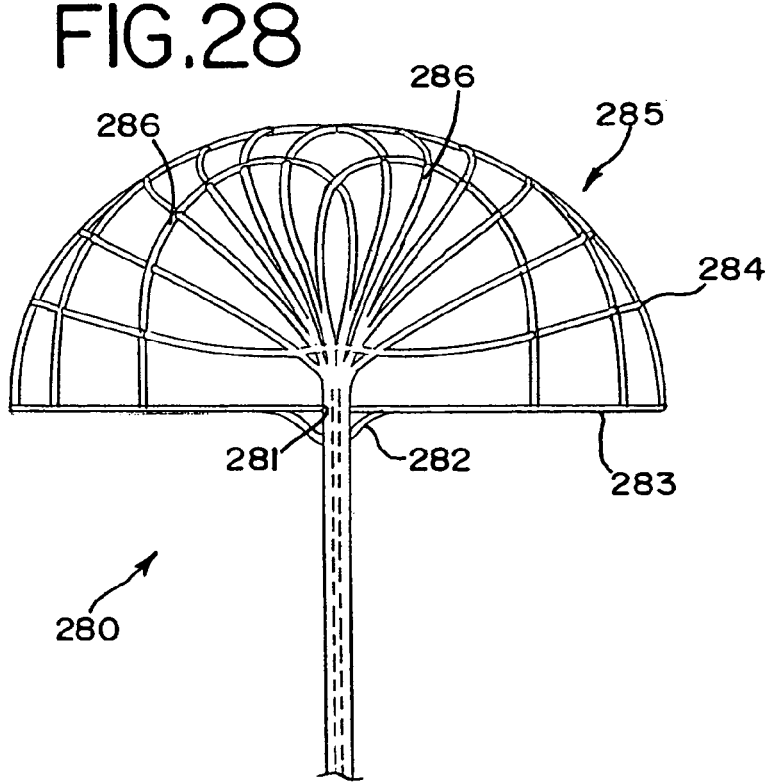

FIGS. 27 and 28 depict two additional embodiments or patterns that may be used to form a basket. Pattern top view FIG. 27 depicts a basket 270 made from 9 pairs 271 of wires, emerging from the vicinity 277 of the control rod, before splitting into individual wires 272. The wires then interleave in the pattern 276 depicted, at junctions 273, 275 and loops 274 before joining the periphery 277. Periphery 277 may have a flex point 278, or may omit the flex point. FIG. 28 depicts a rear view of a basket 280 made from wires or wire pairs that do not split, such as for a very small basket or a basket in which greater stiffness is desired. In this embodiment, a plurality of wires 284 emerges from one area 281 on the periphery, which also has a beak or bend point 282 at about 180°. Wires 284 form an intricate pattern 285 which may include intersections, such as small loops, and interleavings 286. The wires then join at the periphery 283.

Figure 29:
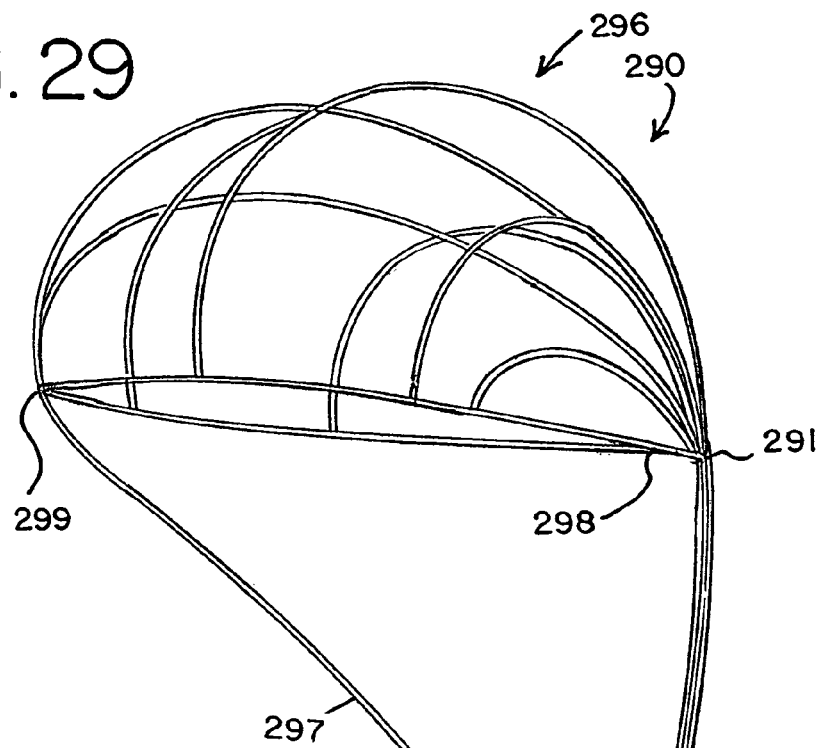
Figure 30:
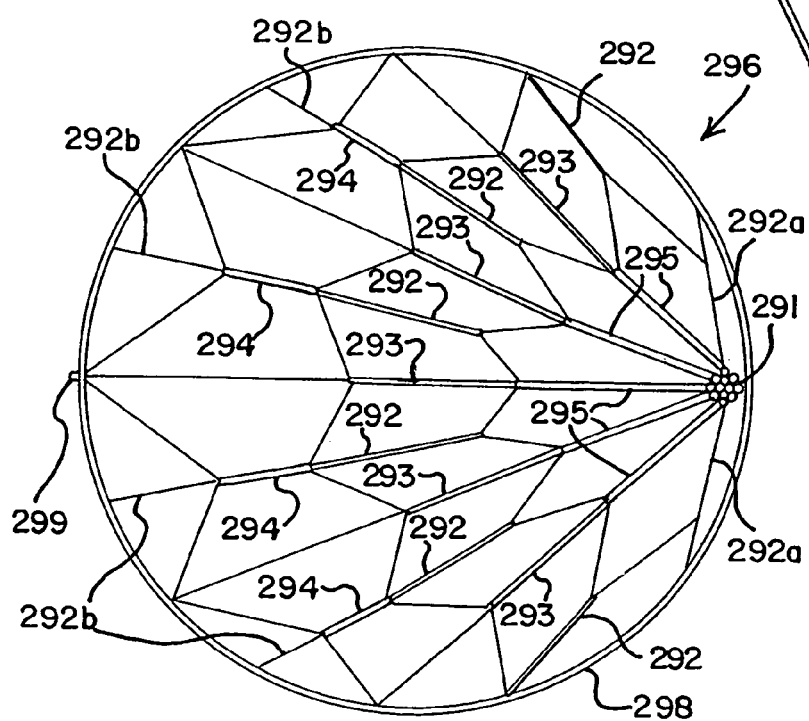

FIGS. 29 and 30 depict another winding pattern which may be useful in embodiments of the present invention. FIG. 29 depicts a side view of a retrieval device 290 with basket 296. Retrieval device 290 includes a plurality of loops gathered at one point 291 of basket 296 for insertion into a cannula or control rod (not shown), and a basket 296. Basket 296 includes a periphery 298 of wires or loops returning to the gathering point 291, and a tethering wire of loop 297. Tethering wire 297 is joined to the control rod or cannula, and also extends to point 299 at about 180° from gathering point 291.

FIG. 30 presents a top view of the embodiment of FIG. 29. In this embodiment, there are about 30 wires, including a single tethering wire 297 shown in FIG. 29. The wires shown in FIG. 30 include a number of wire pairs, and bundles of three, four and five wires, all of which are designated with a numeral and all of which are depicted with a heavier line. Unnumbered, thinner lines in FIG. 30 represent single wires. The wires shown in FIG. 30 include two wire pairs 292a at the right hand side of FIG. 30, and five five-wire bundles 295. As the wires progress from right to left, the two two-wire bundles 292a split into single wires, one wire of each of which joins periphery 298, and the other wire proceeding to a second two-wire bundle, or wire pair 292. The five-wire bundles each split into two single wires and a three-wire bundle 293. Three-wire bundles 293 then split into three single wires, one or more of which is routed to periphery 298 or to one or more four-wire bundles 294. Four-wire bundles 294 then split into wire pairs 292b or single wires, all of which are routed to periphery 298. The previously-described embodiments of the ureteral backstop filter and retrieval device have been found to more easily release stones and calculi from the basket. Embodiments such as those in FIGS. 29 and 30 also tend to allow greater control of the basket.

The invention has been described in terms of embodiments useful especially in removing kidney stones and fragments of kidney stones. The invention contemplates structures comprising and consisting of the embodiments shown in the figures and described in the text. Other embodiments may be used in vascular service, for instance, for removing emboli or thrombi from blood vessels. Instead of being deployed with an endoscope, a surgeon may use vascular embodiments in combination with, for instance, an angioplasty catheter or stent delivery system. As noted above, the sheath for the retrieval device may be as narrow as 3 Fr (1 mm) or even narrower, thus making the retrieval device easy to employ. Other embodiments may be used in other applications and other areas of the body, such as embodiments useful for removing gallstones from the bile duct or related areas. These embodiments are not limited to human bodies, but may be used in veterinary service as well.

Accordingly, it is the intention of the applicants to protect all variations and modifications within the valid scope of the present invention. It is intended that the invention be defined by the following claims, including all equivalents. Since the foregoing detailed description has described only a few of the many alternative forms this invention can take, it is intended that only the following claims, including all equivalents, be regarded as a definition of this invention.

What is claimed is:

1. A medical retrieval device, comprising:
   a control rod;
   a basket having a periphery and a filter comprising a plurality of wires having wire ends, wherein each wire of the plurality of wires defining the filter is interleaved with another wire of the plurality of wires, and each wire of the plurality of wires defining the filter is twisted together with at least one other wire of the plurality of wires defining the filter within a first portion of the filter and each wire of the plurality of wires separates into a single wire in a second portion of the filter, wherein the wire ends are each jointed together into a wire bundle at one or more points proximal to the periphery, wherein the periphery is defined by a first loop that traverses a portion of the periphery and a second loop that traverses a different portion of the periphery, the first and second loops are linked together at a joint located at a distal end of the basket, and wherein the plurality of wires defining the filter join the periphery at points located between the wire bundle and the joint;
   wherein the control rod connects to or comprises the wire bundle; and
   a sheath being moveable with respect to the basket for retracting and extending thereof, wherein the basket asymmetrically projects in one direction from the sheath when the sheath is in a retracted position.

2. The device of claim 1, wherein the device further comprises an echogenic surface or radiopaque component.

3. The device of claim 1, wherein the basket has a proximal end substantially opposite from the distal end, and the basket defines a flex point near the distal end.

4. The device of claim 1, wherein the wire bundle connects to the control rod with at least one of a crimp, a weld joint, a braze joint, a solder joint, and an adhesive.

5. The device of claim 1, further comprising a removable handle.

6. The device of claim 1, further comprising a removable handle having a first end and a second end, the first end attached to the sheath and the second end attached to the control rod.

7. The device of claim 1, wherein the basket in an extended position is in a form selected from the group consisting of a concave hemisphere, a convex hemisphere, a cylinder, a sphere, a cone, a saucer, an umbrella, and an irregular shape.

8. The device of claim 1, further comprising at least one stop on the control rod or the sheath.

9. The device of claim 1, further comprising a radiopaque marker.

10. The device of claim 1, wherein the loops are made from a material selected from the group consisting of Nitinol and a shape memory alloy.

11. The device of claim 1, wherein the link between the two or more wire loops defining the periphery is at a flex point.

12. The device of claim 1, wherein the wire bundle comprises twisted wires.

13. The medical device of claim 1, wherein each wire of the plurality of wires defining the filter is interleaved with another wire of the plurality of wires defining the filter in the second portion of the filter.

14. The device of claim 13, wherein the filter further comprises a mesh defined by the plurality of interleaved wires in the second portion of the filter.

15. The device of claim 1, further comprising a filiform tip formed from at least one wire of the plurality of wires.

16. The device of claim 1, further comprising a connector between the wire bundle and the control rod.

17. The device of claim 1, further comprising a connector with a notch between the plurality of wires and the control rod.

18. A ureteral backstop filter device, comprising:
   a control rod comprising an attaching portion and a control portion;
   a basket having an atraumatic periphery defining an opening into the basket significantly larger than any other openings into the basket and a filter, the basket comprising a plurality of wires having wire ends, wherein each wire of the plurality of wires is interleaved with at least one other wire of the plurality of wires, and each wire of the plurality of wires defining the filter is twisted together with at least one other wire of the plurality of wires within a first portion of the filter and each wire of the plurality of wires separates into a single wire in a second portion of the filter, wherein each wire of the plurality of wires defining the filter is interleaved with another wire of the plurality of wires in the second portion of the filter,
   wherein the wire ends are each jointed together into a wire bundle at one or more points proximal to the periphery, wherein the periphery is defined by a first loop that traverses a portion of the periphery and a second loop that traverses a remaining portion of the periphery not traversed by the first loop, the first and second loops are linked together, and each of the wires defining the plurality of wires join the periphery remotely from the wire bundle and the joint;
   wherein the wire bundle is attached to the control rod, wherein the periphery further comprises a flex point defined by the link between first and second loops;
   a sheath being moveable with respect to the basket for retracting and extending thereof, wherein the sheath contains the basket, wherein when the sheath is retracted or the basket is extended, the basket projects perpendicularly from the sheath.

19. The device of claim 18, wherein the basket has a proximal end and a distal end, and the flex point is near the distal end.

20. The device of claim 18, wherein at least a component of the device is radiopaque or echogenic.

21. The device of claim 18, wherein the attaching portion is radiopaque.

22. The device of claim 18, wherein the plurality of wires and first and second loops are made from a material selected from the group consisting of Nitinol and a shape memory alloy.

23. The device of claim 18, wherein the plurality of wires and first and second loops are made from a superelastic alloy and are in a relaxed condition when the basket is deployed.

24. The device of claim 18, wherein the wire bundle is secured to the control rod with at least one of a crimp, a weld joint, a solder joint, a braze joint, and an adhesive.

25. The device of claim 18, further comprising a removable handle.

26. The device of claim 18, wherein a cross-section of the basket has a shorter axis and a longer axis.

27. The device of claim 18, further comprising a stop on the control rod or the sheath.

28. The device of claim 18, further comprising a radiopaque component.

29. The device of claim 18, wherein the first and second loops are twisted together.

30. The device of claim 18, wherein at least one of the first and second loops is bent.

31. A retrieval device, comprising:
a control rod;
a basket having an atraumatic periphery defining an opening into the basket significantly larger than any other opening into the basket and a filter comprising a plurality of superelastic wires having wire ends, wherein each wire of the plurality of wires defining the filter is interleaved with another wire of the plurality of wires and each wire of the plurality of wires is twisted together with at least one other wire of the plurality of wires within a first portion of the filter and each wire of the plurality of wires separates into a single wire in a second portion of the filter, wherein the wire ends are each jointed together into a wire bundle at one or more points proximal to the periphery, wherein the plurality of wires define a tipless filter;
wherein the periphery is defined by a first twisted loop that traverses a portion of the periphery and a second twisted loop that traverses a remaining portion of the periphery not traversed by the first loop, the first and second of the plurality of loops are linked together at a joint, and a portion of each wire of the plurality of wires joins the periphery remotely from the wire bundle and the joint;
a filiform formed from at least a portion of the superelastic wire loops;
a sheath being moveable with respect to the basket for retracting and extending thereof, wherein when the sheath is retracted or the loops are extended, the basket projects perpendicularly from the sheath, the loops being in a relaxed condition when outside the sheath.

32. The device of claim 31, wherein the periphery further comprises a flex point defined by the link between the first and second twisted loops.

33. The device of claim 31, further comprising a removable handle.

34. The device of claim 31, wherein the basket further comprises a filter mesh defined by the first and second portions of the filter.

35. The device of claim 31, further comprising a stop on the control rod or the sheath.

36. The device of claim 31, further comprising at least one component that is radiopaque or echogenic.

37. The device of claim 31, further comprising a filiform tip.

38. A retrieval device, comprising:
a control rod;
a basket having an atraumatic periphery defining an opening in the basket significantly larger than other openings and a filter, the basket comprising a plurality of wires and first and second loops jointed together at a single point and attached to the control rod, at least a part of each of the plurality of wires being interleaved with each other and joining the atraumatic periphery of the basket, and each wire of the plurality of wires defining the filter is twisted together with at least one other wire of the plurality of wires defining the filter within a first portion of the filter and each wire of the plurality of wires separate into a single wire in a second portion of the filter, wherein the periphery is defined by a first twisted loop that traverses a portion of the periphery and a second twisted loop that traverses a remaining portion of the periphery not traversed by the first loop, the first and second loops are linked together to define a flex point located at a distal end of the periphery; and
a sheath being moveable with respect to the basket for retracting and extending thereof, wherein the basket asymmetrically projects in one direction from the sheath when the sheath is in a retracted position.

39. A medical retrieval device, comprising:
a control rod;
a basket having a periphery defining an opening in the basket significantly larger than other openings and a filter comprising a plurality of wires jointed together at their wire ends to form a wire bundle at the periphery, the wire bundle being routed to the control rod for joining thereto at a distal end of the control rod, and at least a part of each wire of the plurality of wires is interleaved with other wires of the plurality of wires, and each wire of the plurality of wires defining the filter is twisted together with at least one other wire of the plurality of wires defining the filter within a first portion of the filter and each wire of the plurality of wires separate into a single wire in a second portion of the filter, wherein the periphery is defined by a first twisted loop that traverses a portion of the periphery and a second twisted loop that traverses a remaining portion of the periphery not traversed by the first loop, the first and second loops are linked together to define a flex point, and each wire of the plurality of wires joins the periphery remotely from the wire bundle; and
a sheath being moveable with respect to the basket for retracting and extending thereof, wherein the basket asymmetrically projects in one direction from the sheath when the sheath is in a retracted position.

40. The device of claim 1, wherein the first and second loops are each twisted.

* * * * *